(12) United States Patent
Anderson

(10) Patent No.: US 6,269,265 B1
(45) Date of Patent: Jul. 31, 2001

(54) APPARATUS AND METHOD FOR EVOKING AND CAPTURING A SWEAT SAMPLE

(75) Inventor: Paul J. Anderson, Hudson, WI (US)

(73) Assignee: WR Medical Electronics Co., Stillwater, MN (US)

(*) Notice: Subject to any disclaimer, the term of this patent is extended or adjusted under 35 U.S.C. 154(b) by 0 days.

(21) Appl. No.: 09/510,024

(22) Filed: Feb. 22, 2000

Related U.S. Application Data

(60) Provisional application No. 60/120,900, filed on Feb. 22, 1999.

(51) Int. Cl.$^7$ .................................................. A61N 1/30
(52) U.S. Cl. .................................................. 604/20
(58) Field of Search ................ 604/20, 22, 890.1, 604/891.1, 892.1, 304–308, 23, 24, 25, 26; 600/573, 575, 578, 580; 73/23.2, 23.22

(56) References Cited

U.S. PATENT DOCUMENTS 4,266,556 * 5/1981 Barlow et al. ..................... 128/760
4,398,543 * 8/1983 Sandlin et al. ..................... 128/760

* cited by examiner

Primary Examiner—Manuel Mendez
(74) Attorney, Agent, or Firm—Fredrikson & Byron, P.A.

(57) ABSTRACT

An apparatus and related method for evoking, capturing, and optionally measuring one or more parameters within a sweat sample on the surface of the skin. The apparatus includes the use of an iontophoresis chemical chamber adapted to evoke a sweat sample, the chemical chamber being matably attached to a skin capsule adapted to contain the evoked sample. The skin capsule, in turn, is provided with one or more sensors to permit the on site determination of a corresponding number of parameters within the sample.

12 Claims, 13 Drawing Sheets

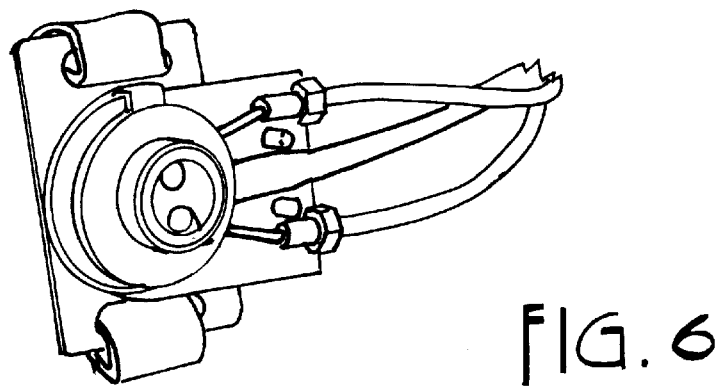
FIG. 6
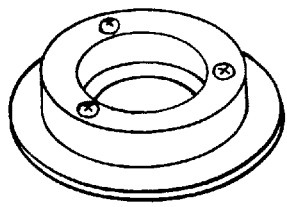
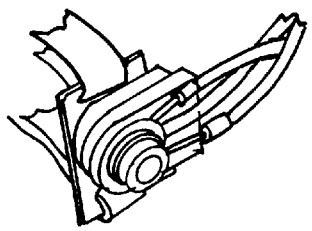
FIG. 7
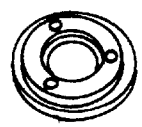
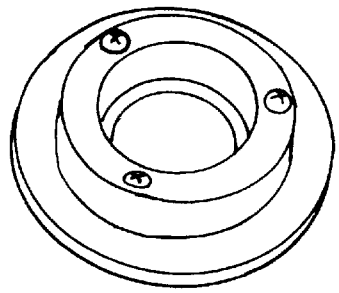
FIG. 8

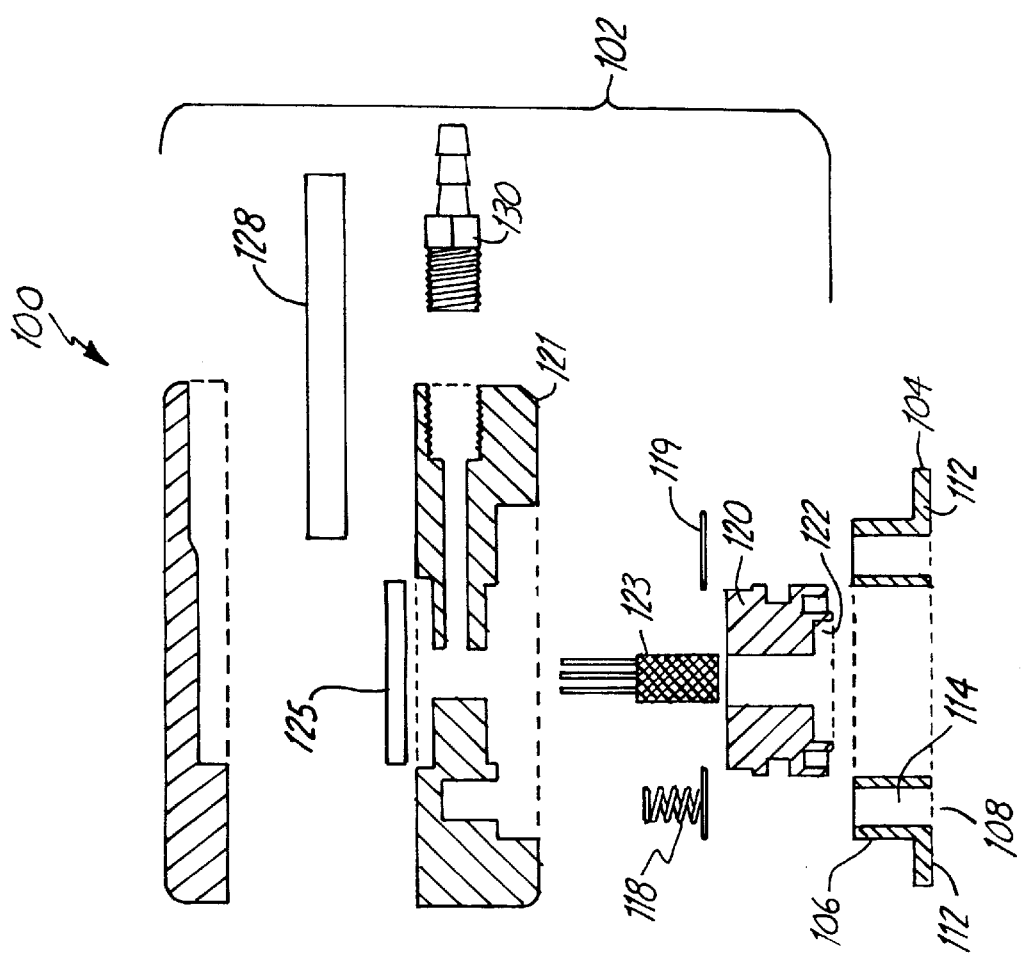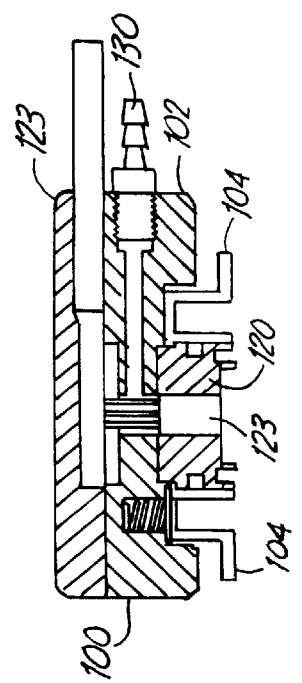

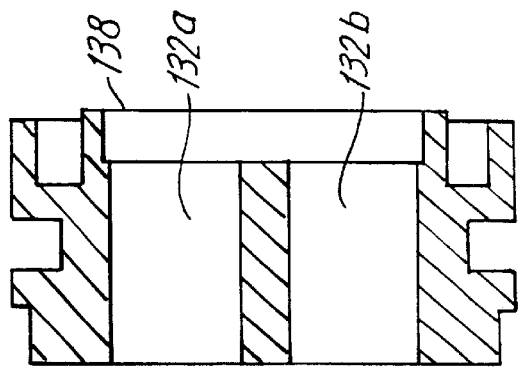
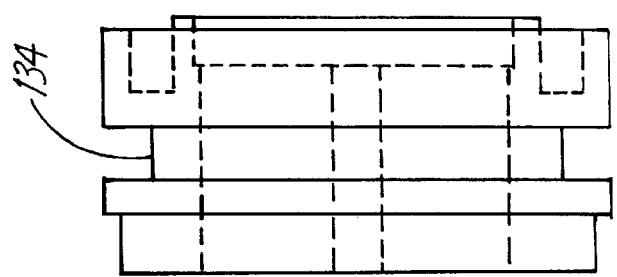
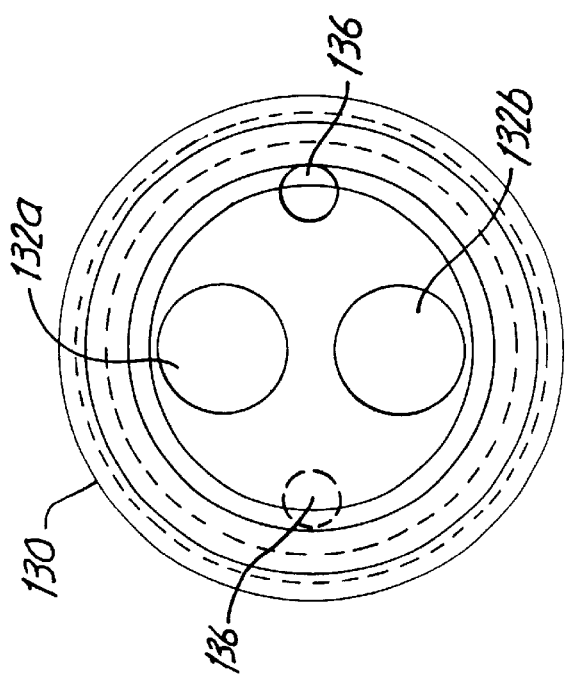

APPARATUS AND METHOD FOR EVOKING AND CAPTURING A SWEAT SAMPLE

CROSS-REFERENCE TO RELATED APPLICATIONS

This application is a continuation-in-part of provisional application having U.S. Ser. No. 60/120,900, filed Feb. 22, 1999, the entire disclosure of which is incorporated herein by reference.

BACKGROUND OF THE INVENTION

1. Field of the Invention

The present invention relates, generally, to medical testing apparatus and methods. More particularly, the invention relates to an iontophoreses device for evoking and measuring a sweat response. The invention has particular utility in measuring the rate and volume of the evoked sweat output for studies of a patient's autonomic nervous system.

2. Background Information

The state of the art includes various devices and methods for evoking and capturing a sweat sample.

Such samples are particularly useful, for instance, in the diagnosis of cystic fibrosis (CF). Cystic fibrosis is one of the most common genetic diseases among Caucasians and is a contributing factor in causing suffering among children and adults. CF affects the mucus-producing glands and other exocrine glands in the body. Clinically, CF is characterized by chronic respiratory infections and obstructive lung disease, pancreatic gland insufficiency leading to an inability to digest fats, male infertility and abnormally high levels of electrolytes in the sweat.

The sweat gland defect in CF has been well characterized for years and is presently used to help diagnose CF, by the use of a "pilocarpine iontophroesis sweat test". Sweat production is stimulated through two pathways: the cholinergic pathway and by the adrenergic/sympathetic pathway (i.e., fight or flight response). Thus, sweat production can be stimulated by both cholinergic and adrenergic agonists. It is the collection of cholinergic stimulated sweat, using the cholinergic agonist pilocarpine, and the subsequent measurement of sweat chloride concentration, that forms the basis of standard diagnostic testing for cystic fibrosis (CF).

Samples of sweat may be collected in various ways. The most common method used today is to introduce pilocarpine nitrate into the skin by iontophoresis, a process in which an electrical current is delivered through the skin between a pair of electrodes attached to the skin. Generally, current flow is continued for about 15 minutes, after which the electrodes arc removed and a collection cup is placed over the area of the skin where the pilocarpine nitrate has been administered. After approximately 15 minutes, the sweat that has formed on the skin under the cup is collected into the cup by scraping the cup across the skin. Normally the collection cup is at room temperature, which is a temperature below normal body and skin temperature.

Stimulation of sweat production with pilocarpine leads to initial production of an isotonic secretion in the sweat gland. In non-CF patients, as the secretion traverses the sweat duct, chloride is reabsorbed. This leads to low concentration of chloride in sweat as it appears on the skin. This chloride resorption is dependent on the presence of a functional CF related gene (known as "CFTR"). In CF patients, who lack functional CFTR, the sweat chloride concentration remains high, and distinguishes most, but not all, CF from non-CF patients. However, this technique does not distinguish heterozygote carriers of CFTR mutations from non carriers, nor does the sweat chloride concentration correlate with disease severity. Furthermore, the pilocarpine test involves the use of a sweat test apparatus consisting of electrodes and a voltage source and the use of specially trained personnel. These methods require the elution of the sweat electrolytes collected on the pads and determination of chloride content of the sweat. While this method remains the "gold standard", it occasionally yields ambiguous results. Therefore, it would be useful to have an alternative or better method of diagnosing CF.

In one approach, U.S. Pat. No. 4,266,556 (Barlow, et al. May 12, 1981) describes a sweat collection device for use with equipment for inducing sweat has a cup member that is electrically heated and in which the temperature of the cup is maintained substantially constant by temperature monitoring and controlling supply of electrical power to the cup in accordance with the requirements determined by the temperature monitoring.

In another approach, U.S. Pat. No. 4,398,543 (Sandlin, et al. Aug. 16, 1983) describes a moisture collecting chamber having a probe which engages the skin to form a seal between the probe and the skin surface which is being tested and to provide a substantially uniform force when the probe is positioned on a patient. A connecting mechanism is attached to the probe and limiting means is mounted with the probe to provide uniform pressure of the probe against the skin surface during each test.

Various other sweat test devices have been described or arc in current use. For instance, Abrams Instrument Corporation markets a device known as the "Abrams Model WVD-101 Evaporative Water Loss Instrument". The Abrams device is a "single channel" system that uses an air-perfuse capsule, sealed to the skin surface, to measures the rate of water evaporation from that surface.

Yet other known devices or approaches include, the Wescor Sweat Check Conductivity Analyzer which employs iontophoresis using a pilocarpine gel disc to evoke sweat and collects the sweat in a concave chamber to be examined or tested. See also the Chloride Test Patch System from Medtronic, which employs iontophoresis using a pilocarpine interface pad to evoke sweat. A test patch is placed over the area of seating to collect and analyze the sample for chloride concentration. While each such device typically uses iontophoresis to evoke a sweat response, and measures at least one characteristic or parameter of the sweat evoked, they tend to differ in several respects as well, including the fact that they generally do not permit the measurement of both the rate and volume of sweat produced. Rather, they tend to concentrate on the concentration of sodium in the sweat itself, in their relatively limited roles as a screening tools for CF. Nor do they tend to provide either a chamber to contain moisture vapor upon the skin, or in turn, one or more sensors to measure corresponding parameters within the chamber, while in its position upon the skin.

Generally, quantitative sudomotor axon reflex testing methods have been previously described and have well accepted roles in medical diagnosis. See, for instance, Low, PA, et al., "Standardization of Autonomic Function", Chapter 23, pp. 287–295 in *Clinical Autonomic Disorders*, $2^{nd}$, ed. Lippincott-Raven Publishers (1997). It appears to be the corresponding apparatuses themselves that are in need of improvement.

The devices and methods of the known art are believed to have significant limitations and shortcomings. Specifically, the devices and methods of the known art use a bottle of pressurized nitrogen gas or another pressurized gas source as a dry vapor source. Additionally, the devices and methods of the known art do not have the small and compact sensors positioned in the skin capsule, including temperature and humidity sensors, mass airflow sensors, a humidity sensor, and an absolute pressure sensor. The devices and methods of the known art also lacked a voltage sensitive orifice within the main enclosure of the device to control and prepare the dry air for circulation out to the collection capsule affixed on the skin. Furthermore, known sweat testing devices lack a donut-shaped stimulating agent gel that snaps onto the sweat sample collection capsule to evoke sweat for purposes of measuring resting and evoked moisture emission.

The present invention provides an apparatus and method for evoking and capturing a sweat sample which is believed to constitute an improvement over the known art.

BRIEF DESCRIPTION OF THE SEVERAL VIEWS OF THE DRAWING

FIG. 6 is a perspective view of the top of a chemical chamber.

FIG. 7 is another perspective view of the top of the chemical chamber of FIG. 6.

FIG. 8 is a perspective view of the top side of the chemical chamber of FIG. 6.

FIGS. 18a and 18b are exploded and assembled side views, respectively, of preferred capsule and chamber components of this invention.

FIGS. 19a through 19c show bottom, side and side cross-sectional views, respectively, of a preferred skin capsule of this invention.

SUMMARY OF THE INVENTION

Figure 1:
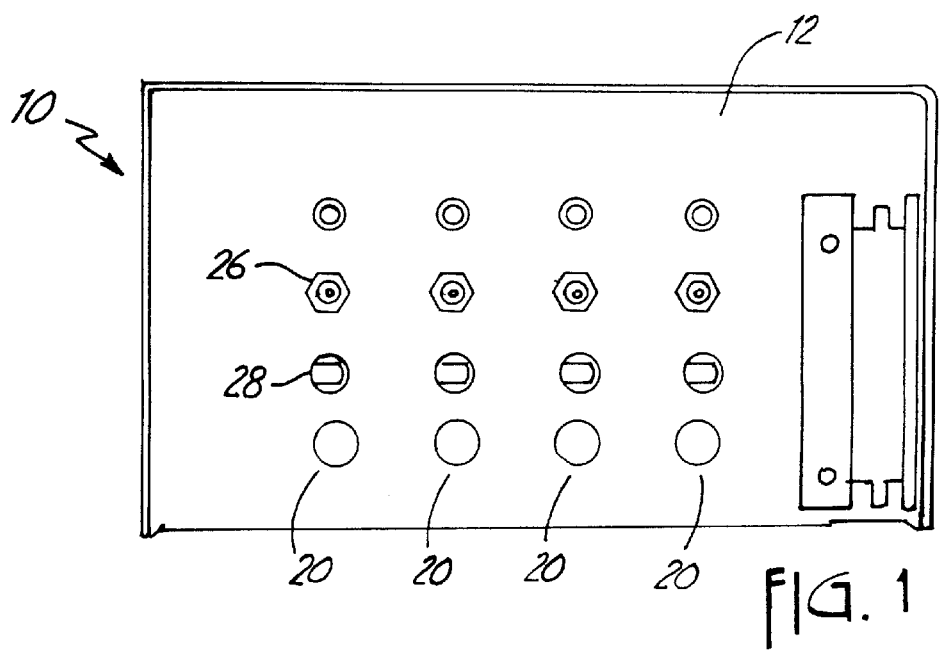
FIG. 1 is a front planar view of the main unit of the present invention.
Figure 2:
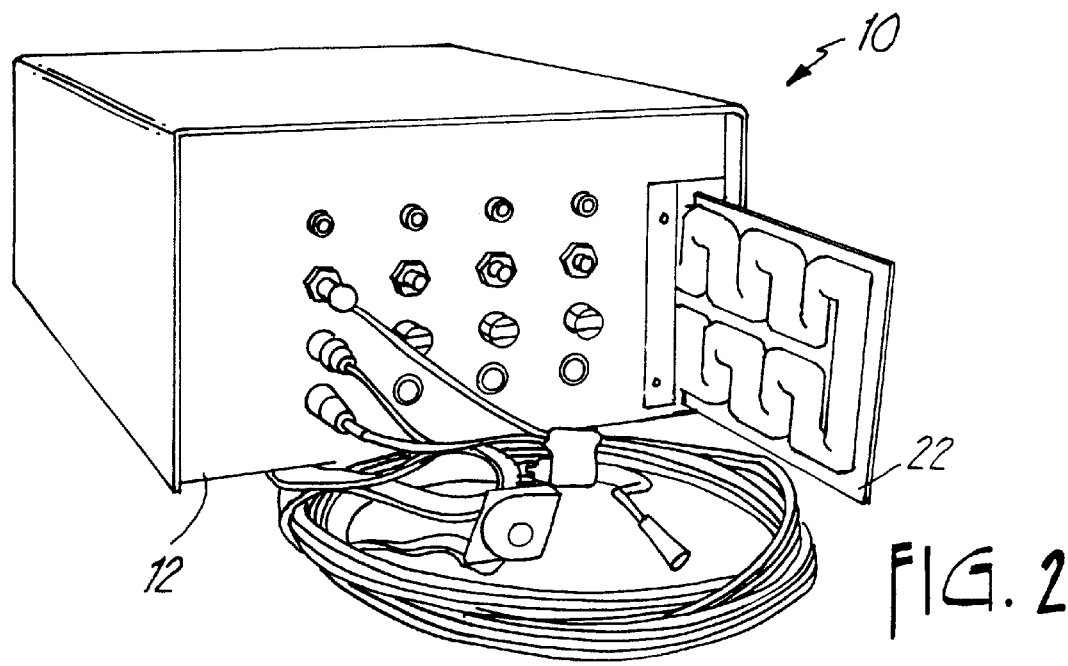
FIG. 2 is a perspective view of the main unit shown in FIG. 1.
Figure 3:
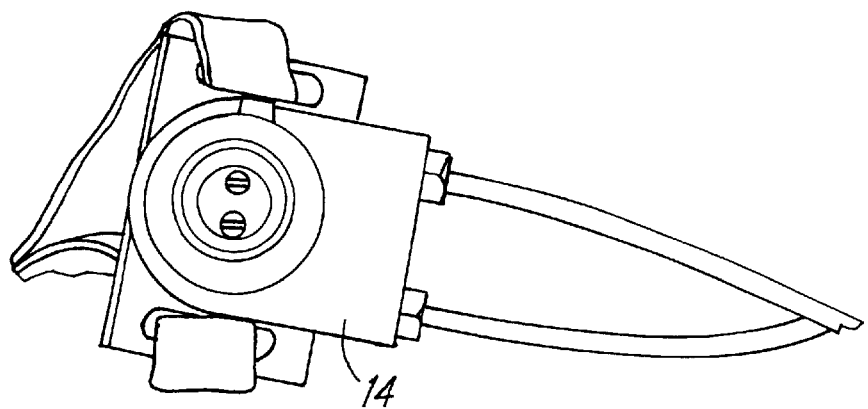
FIG. 3 is a perspective view of the bottom of a skin capsule.
Figure 4:
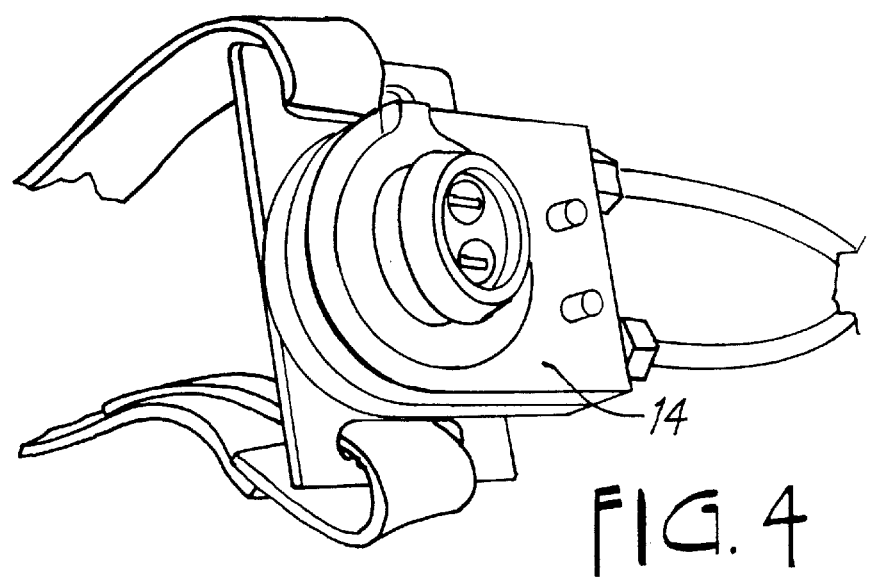
FIG. 4 is another perspective view of the bottom of the skin capsule of FIG. 3.
Figure 5:
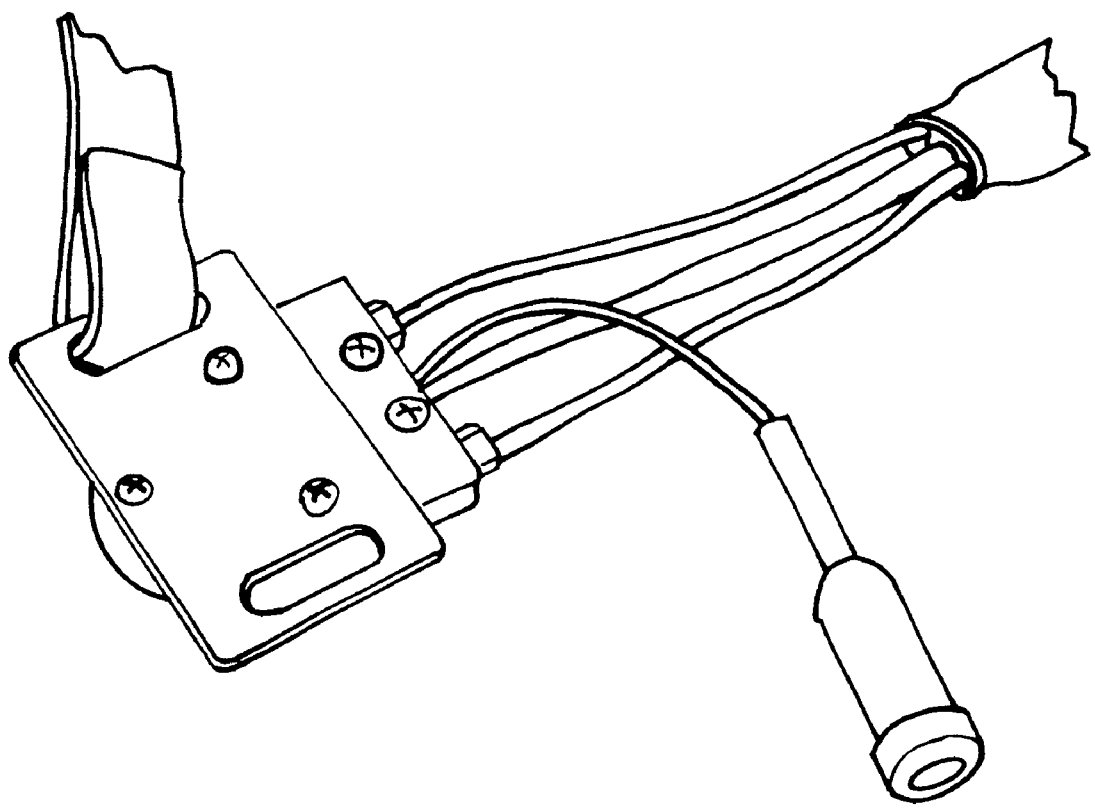
FIG. 5 is a perspective view of the top of the skin capsule of FIG. 3.
Figure 9:
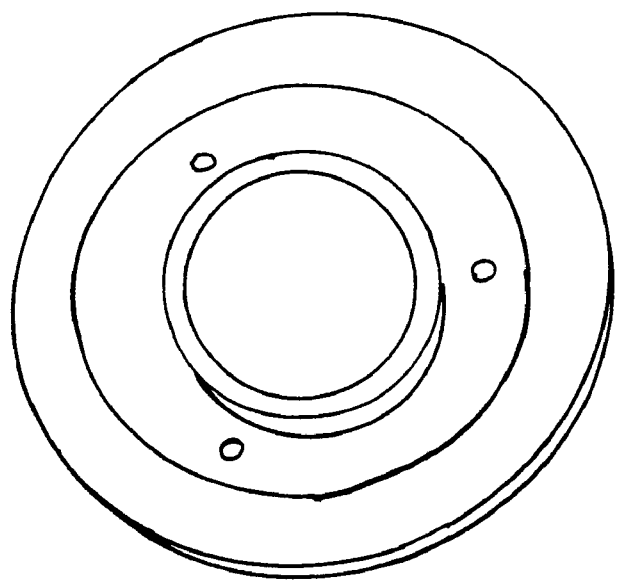
FIG. 9 is a perspective view of the bottom side of the chemical chamber of FIG. 6.
Figure 10:
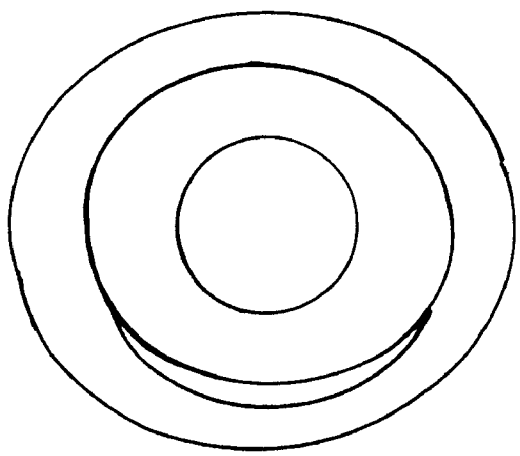
FIG. 10 is a bottom view of the chemical chamber of FIG. 6.
Figure 11:
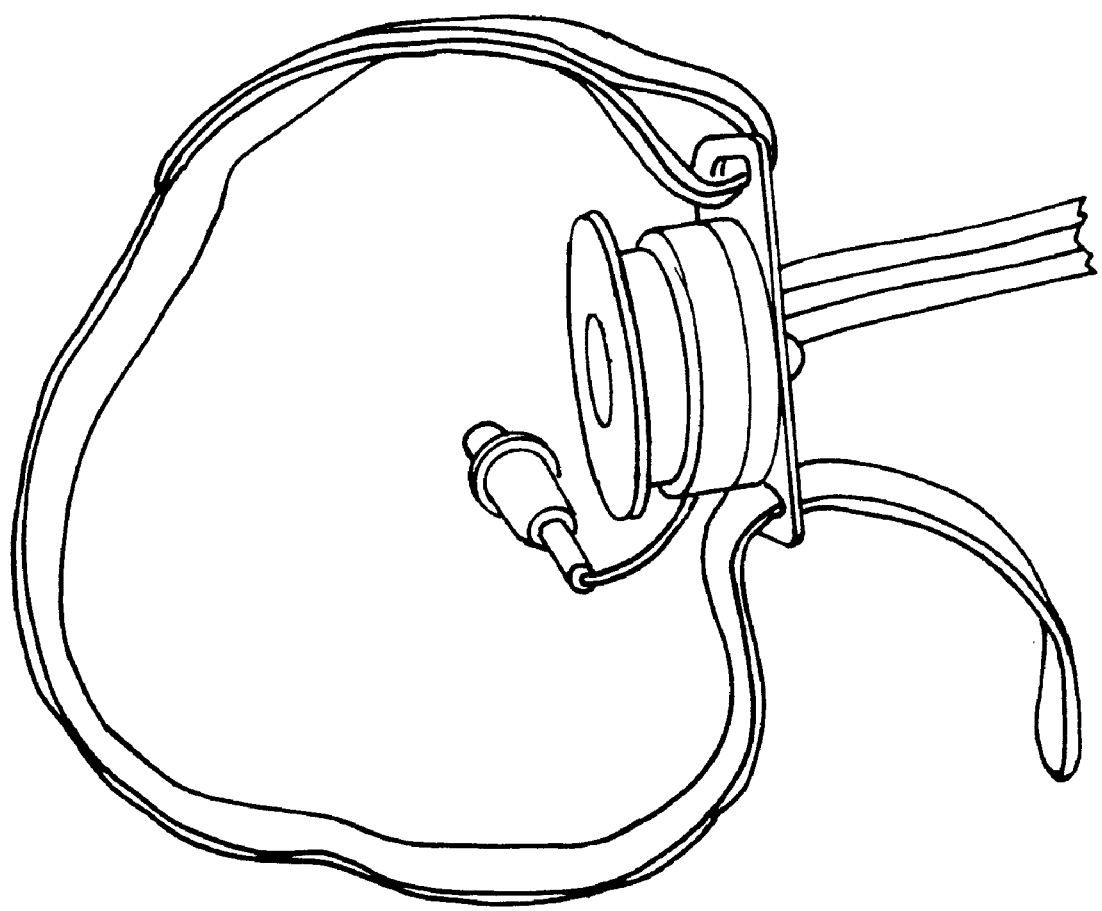
FIG. 11 is a perspective side view of the chamber/capsule assembly.
Figure 12:
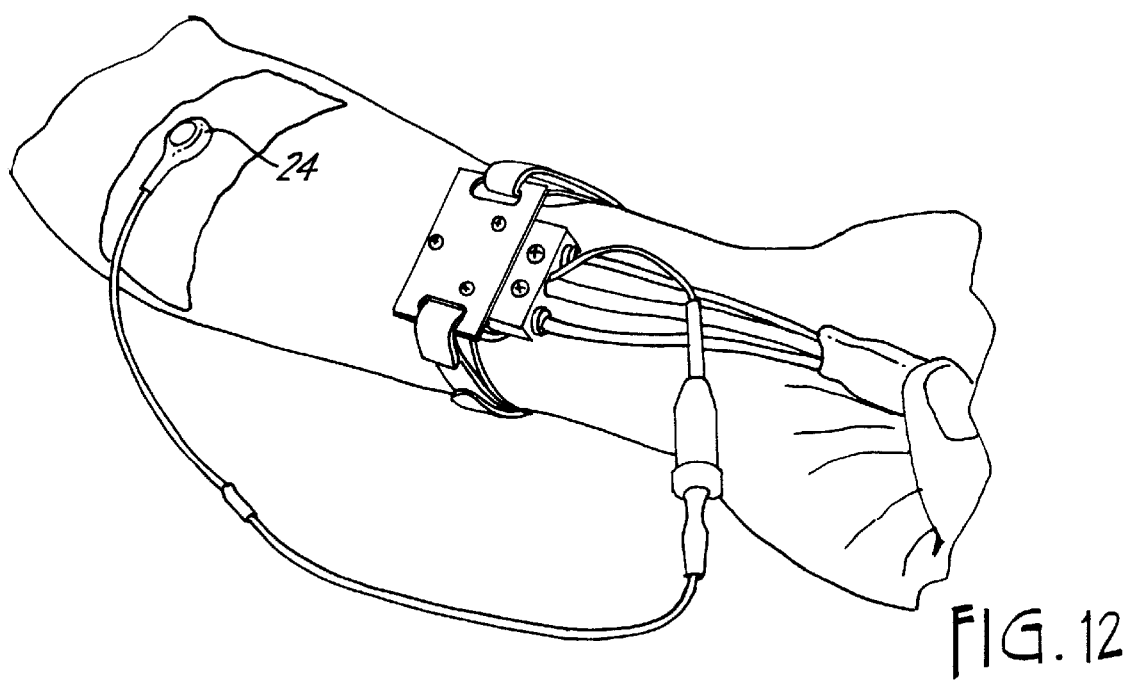
FIG. 12 is a perspective view of the chamber/capsule assembly attached to a patient.
Figure 13:
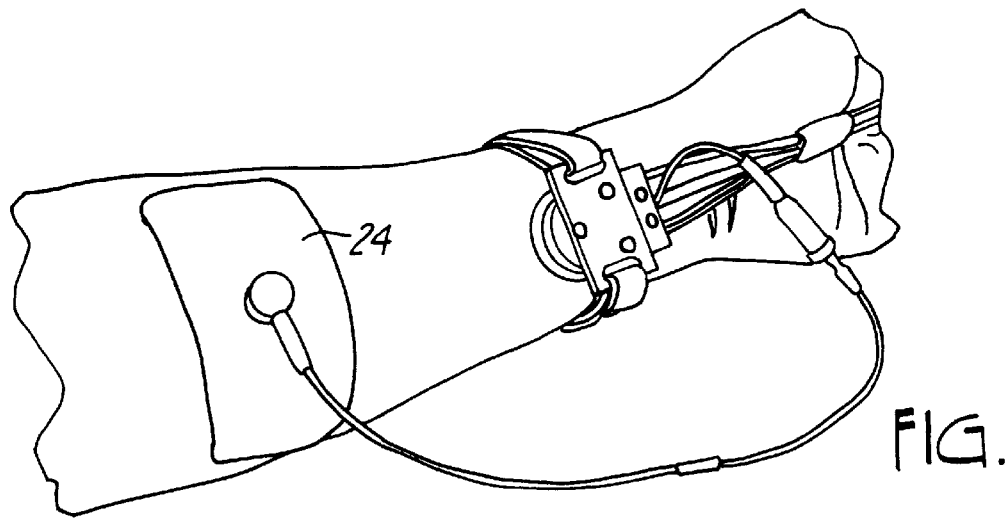
FIG. 13 is another perspective view of the chamber/capsule assembly of FIG. 12 attached to a patient.
Figure 14:
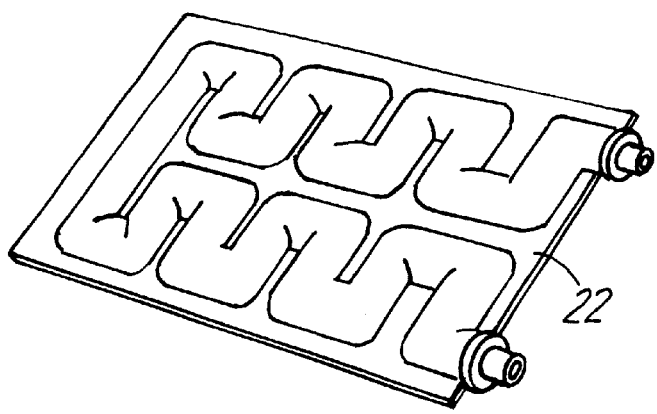
FIG. 14 is a perspective view of the desiccant pack.
Figure 15:
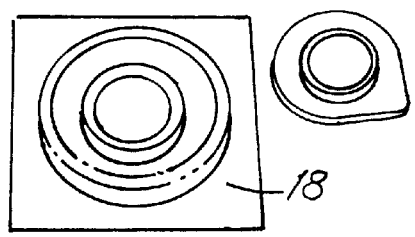
FIG. 15 is a top view of the parking fixture with a cover removed.
Figure 16:
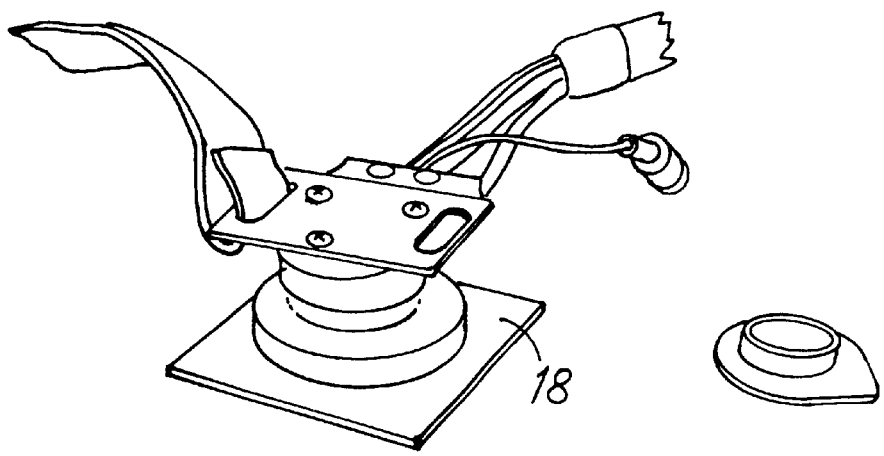
FIG. 16 is a perspective view of the capsule affixed to the parking fixture of FIG. 15.

The present invention provides an apparatus and related method for evoking, capturing, and optionally measuring one or more parameters within a sweat sample on the surface of the skin. The apparatus includes the use of an iontophoresis chemical chamber adapted to evoke a sweat sample, the chemical chamber being matably attached to a skin capsule adapted to contain the evoked sample. The skin capsule, in turn, is provided with one or more sensors to permit the on site determination of a corresponding number of parameters within the sample.

In one preferred embodiment, the present invention provides an apparatus for evoking and capturing a sweat sample and is particularly useful for testing sudomotor axon reflex. The apparatus generally comprises a controller box or main unit, at least one skin capsule, an iontophoretic chemical chamber for each skin capsule, a parking fixture for each available channel, one "wet" cell, a removable, disposable desiccant chamber for each parking fixture, and an iontophoretic stimulator grounding pad for each skin capsule. There are preferably four skin capsules that correspond to four available channels in the main unit. The main unit is electrically connected to a personal computer. ATLAS (Autonomic Testing Lab and Acquisition System) application software operating on the computer controls the operation of the reading and processing of moisture measurement information provided by the main unit, including flow in, flow out, temperature, humidity, desiccant humidity, and atmospheric pressure. The software then calculates the sweat rate and total sweat volume.

Features of the invention include the incorporation of an integral dry air source, an RS-232 interface, disposable stimulator capsules, self-calibrating capabilities, and highly accurate and repeatable measurements. The system is convenient to operate and easily interfaces to personal computers. No special gases are needed to operate the system.

The features, benefits and objects of this invention will become clear to those skilled in the art by reference to the following description, claim(s), if any, and drawings.

DETAILED DESCRIPTION

The present invention provides an apparatus and method for evoking, capturing, and optionally measuring one or more parameters within a sweat sample, the apparatus comprising, a) at least one skin capsule, and preferably a plurality of skin capsules (e.g., four identical skin capsules), each comprising
  i) a capsule chamber adapted to be removably positioned in sealed contact with the skin, in order to contain sweat evoked from the underlying skin,
  ii) one or more sensors operably connected to the capsule chamber and adapted to measure corresponding parameters (e.g., humidity, temperature) within the capsule chamber itself,
  iii) gas inlet and outlet conduits adapted to controllably deliver desiccated gas (e.g., air) and recover gas (e.g., humidified with sweat) from the capsule chamber, respectively, and
  iv) an electrical contact adapted to receive electrical energy from a controller in order to deliver the energy to a corresponding iontophoretic active electrode contact,
b) at least one iontophoretic chemical chamber, and preferably a number equal to the number of skin capsules, each chemical chamber preferably comprising i) a biocompatible polymeric material forming a chamber adapted to be removably retained upon the skin of a patient (e.g., made from biocompatible polymer such as polyethylene terephthalate and having an adhesive backing), ii) a stimulating agent stably retained within the chemical chamber (e.g., in the form of a gel containing acetylcholine or pilocarpine) in a manner that permits the agent to be make iontophoretic contact with the skin, and iii) an iontophoretic active electrode contact (e.g., grounding electrode in the form of a rewettable hypoallergenic hydrogel approved for use on humans), adapted to make contact with the electrical contact of the skin capsule, in order to form an active electrode for the delivery of stimulating agent from the chemical chamber and to the skin, each chemical chamber being adapted to be affixed to a skin capsule (i.e., fixedly matable with the skin capsule) in a manner that permits the resultant capsule/chemical chamber assembly to be operated in order to be positioned upon and evoke a sweat response from the skin, by iontophoretic delivery of the stimulating agent, and adapted, in turn, to contain a known volume of the sweat evoked, in the form of moisture within the capsule chamber, and c) a controller adapted to control and coordinate the operation of the apparatus, including the iontophoretic chemical chamber and sensors.

Optionally, and preferably, the apparatus further comprises:

d) at least one "wet cell" adapted to permit comparison to a known humidity standard, in order to calibrate the apparatus, e) a number of storage (also known as "parking") fixtures equal to the number of skin capsules plus wet cells, each parking fixture adapted to hold either a chamber in a desiccated environment or to hold a wet cell, respectively, and f) at least one return (inactive) electrode, containing an electrolyte solution and adapted to be positioned upon the patient's skin, preferably in an area remote from the chemical capsule (and active electrode), in order to permit iontophoresis of the stimulating agent by the application of direct current to the active electrode.

The apparatus employs iontophoresis to evoke a sweat sample, and to also measure the amount (including rate and/or volume) of moisture (water) within a small chamber affixed to the skin. As such, the apparatus provides a variety of new and useful features, as well as corresponding opportunities. For instance, in a preferred embodiment, the apparatus provides the use of one or more desiccant packs (as opposed to conventional nitrogen gas sources) to maintain the capsule in a dry state. Also, a preferred apparatus can incorporate the simultaneous use of one or more, and preferably several different sensors, each adapted to function adjacent or within a closed chamber at the measuring site itself.

In a related method, the apparatus and system of this invention can be used in a method that measures the resting sweat output and evoked sweat output, both in terms of both rate and volume. These measurements, in turn, can be used by the physician to study the patient's autonomic nervous system, e.g., in connection with medically accepted tests and diagnostic procedures.

In order to calculate the amount of humidity (moisture) within the capsule, the system permits the measurement of both temperature and relative humidity. Using valves provided by the sensors, the actual moisture level can then be determined according to conventional thermodynamic principles, using firmware and software embodied in the computer support.

In a preferred embodiment, the apparatus provides a plurality (and preferably four channels), to permit a corresponding number of individual moisture samples to be obtained simultaneously from a given patient, which in turn, permits the entire procedure to be completed in a suitably short period of time (e.g., within about 30 minutes).

In practice, the controller box, which can itself be operably connected to a computer, provides and/or controls the various power supplies, air source(s) (e.g., air pump), airflow regulator(s), voltage-sensitive proportioning orifice valve(s), mass airflow sensor(s), and source air desiccant pack(s), as well as ports and connectors needed to control and coordinate the activity of the parking fixture, the iontophoresis chamber, and the skin capsule. In its fully assembled operating mode, a preferred apparatus includes both an iontophoresis chamber and a skin capsule in the form of a closed system (e.g., containing a humidity sensor). In use, dry (preferably desiccated) air is pumped through the closed chamber, and the exiting air captured, analyzed (e.g., for flow rate, relative humidity, temperature, vapor pressure), and where appropriate, compared to the incoming air, to determine the concentration of water (i.e., sweat) per unit volume per unit time.

A skin capsule for use in the apparatus of this invention is generally provided in the form of a round disc-like plastic device, which is open on one side (skin side) and which provides a chamber in which the moisture can be captured, so as to be drawn across the temperature and humidity measuring sensors positioned therein. The capsule also provides one or more sensors, e.g., humidity and/or temperature sensors, positioned in a manner that permits them to measure a corresponding attribute of the air or moisture within (e.g., entering and/or leaving) the chamber. Since the capsules will typically include humidity sensors, which will sense any ambient moisture, one or more dry air sources (e.g., desiccant packs) are preferably included in the system as well. Typically, for instance, and the capsules are "parked" on a parking fixture when not in use, which in turn, provides a removable, disposable desiccant chamber.

The skin capsules are adapted to be affixed to the skin with the open side (i.e., chamber) against the skin to permit the moisture sample to be captured therein. The capsule is also provided with an iontophoretic ground contact ("pigtail"), together with associated electrical connectors (e.g., wires) to the controller, to permit an iontophoretic ground pad to be affixed to the capsule in a position sufficiently close to the site of iontophoretic stimulus. The capsule is also provided with tubing for air flow to and from the capsule, preferably integrated into a single cable attached to the chamber. Each capsule is also preferably provided with an attachment means, e.g., a strap employing hook and loop fasteners, to permit the unit to be removably attached to the skin (e.g., arm of the patient)

An iontophoretic chemical chamber of this invention is generally provided in the form of a ring-shaped chamber, open on one side (skin side) and containing a stimulating agent, which in turn, is covered by a removable protective wrapping. The chamber is adapted to be operably attached to a skin capsule, e.g., by screwing or snap fitting the outer wall of the capsule chamber into a sealed relationship within the inner circumference of the chemical chamber. The capsule/chamber assembly, in turn, can be affixed to the skin, in such a manner that the stimulating agent can be iontophoresed into the skin directly surrounding the area being tested. Stimulating agents are preferably in the form of a viscous (e.g., agarose) gel, e.g., containing acetylcholine (e.g., at a concentration of about 0.1M to about 1M) which has been previously poured into the chamber and allowed to solidify. The resulting gel is substantially doughnut shaped, in order to enter the skin in an area surrounding, but not directly over, the area to be measured for sweat response. In use, the protective wrapping can be removed from the chamber, after which the chamber is affixed to a skin capsule, and the chamber/capsule assembly affixed to the patient's skin. The gel remains in the chamber until it is iontophoresed into the skin. The use of a gel in this manner provides a variety of advantages over chemical chambers that contain a stimulating agent in the form of a liquid solution. The chambers are designed to be single-use components, and are properly removed and disposed of after use.

The apparatus of this invention, and its individual components (some of which are believed to be patentable in their own right), can be used in any suitable mode, e.g., for the sole purpose of evoking and measuring a sweat response, and/or for the purpose of delivering a suitable chemical agent to the skin in order to determine the body's sweat response to that agent. In such an embodiment, an inert blank can be used, having substantially the size and shape of the iontophoretic chamber, in order to permit the skin capsule to be used in a similar fashion but without active iontophoresis, simply for the purpose of measuring one or more attributes of sweat evoked by other means.

The apparatus can be used, for instance, to measure various parameters in perspiration brought about by other means, e.g., during exercise or in response to heat stress. The apparatus and method can also be used to quantify psychogenic sweating and to determine the extent of peripheral nerve injuries. Moreover, it can provide data that reveals both static and dynamic hydration characteristics for the skin of individuals. It can also be used to show how different levels of epidermal hydration affect the skin's electrical, mechanical and thermal properties. For instance, an apparatus of this invention can be used in combination with an exercise device, wherein the apparatus is adapted to capture and measure one or more parameters with in sweat produced in the course of exercise. Such an apparatus can be provided in a form adapted to retrofit an existing exercise device, or can be provided as an integral part of an exercise device (e.g., combined into the operator control panel thereof).

Without intending to be bound by theory, it appears that an apparatus of this invention relies upon the postganglionic sympathetic sudomotor axons of the body, which in turn involve a local axon reflex mechanism. During iontophoresis of the stimulating agent the nerve terminals surrounding the sweat gland are stimulated. Impulses pass antidromically along the sympathetic C fibers to branch points, then orthodromically along other sympathetic C fibers to evoke a sweat response. Acetylcholine can be used to stimulate the nerve fibers, which in turn, stimulates the sweat glands directly. The use of pilocarpine, by contrast, is a less effective method for determining the functionality of the nerve fibers. Either stimulating agent can be used in combination with the present apparatus, with the choice being made by the physician depending on the parameters and type of study desired.

The iontophoretic stimulus on/off control is preferably provided in the form of a toggle switch (one for each channel), which provides an indication (e.g., is illuminated) to distinguish its on (activated) vs. off (inactivated) positions. The stimulus amplitude and duration can vary depending on the protocol employed, with the apparatus itself generally providing a constant current (e.g. 2 mA). Conventional protocols of this type are described by Dr. Phillip Low in *Clinical Autonomic Disorders* ($2^{nd}$, ed., Lippincott Raven, 1997). In one such procedure, stimulation is accomplished by the delivery of 2mA current with acetylcholine for 5 minutes. This results in a 10 minute test from which both resting and evoked sweat (rate and volume) can be determined, as well as latency.

Referring to FIGS. 1–21, an example of the preferred embodiment of the present invention is illustrated. As seen in the Drawing, FIGS. 1–17 show various aspects and details of a preferred embodiment of the method and apparatus of this invention. FIGS. 18a and 18b, for instance, show exploded and assembled side views, respectively, of a capsule/chemical chamber assembly 100, including both a skin capsule 102 and a chemical chamber 104. The generally circular chemical chamber includes a raised doughnut shaped portion 106, having at least a portion of its major skin-contacting edge 108 open to the skin. The doughnut shaped portion is concentrically positioned within an outer flange 112 having an adhesive backing (not shown) for use in attaching the chemical chamber to the skin. The raised portion 106 of the chemical chamber also contains an amount of stimulating agent 114, and an electrical contact 116 at its uppermost portion.

The skin capsule 102, in turn, is shown in exploded form in FIG. 18a as including, inter alia, a sensor sampling chamber portion 120, a capsule body 121 and a capsule cover 123. The capsule also provides a corresponding electrical contact 118 adapted (as shown, by a combination of springs and floating metal contacts 119) to provide direct current to the electrical contact 116 of the chamber when the capsule and chamber are mated. The capsule includes a chamber portion 120 having an interior raised chamber formed by internal edge 122. The support is adapted to be connected to capsule body 121, and in turn, to capsule cover 123, e.g., together with associated sensors, contacts, and connectors. Contained within the chamber portion are gas apertures (shown in FIG. 19 as inlet 124a and outlet 124b) apertures. At or near the apertures are positioned one or more sensors (123) for use in measuring one or more corresponding parameters (e.g., temperature, humidity) of the chamber contents, and adapted to be connected to sensor circuit board 125, which is also adapted to be positioned with the assembled capsule. The capsule also provides the attachment point for the various wires and tubing used in its operation, including those shown as electrical connections cable 128 and hose barb 130 for supply and return air flow.

The capsule and its associated chamber are adapted to provide a snug fit between the outer wall of the capsule chamber portion and the inner wall of the doughnut shaped iontophoretic chemical chamber, thus making electrical contact between the corresponding parts 118 and 116 and permitting the iontophoretic delivery of stimulating agent 114 from the chamber through the open face 108. Sweat from the underlying skin, in turn, is contained within the chamber thus formed, permitting the measurement of various parameters by controlled delivery and recovery of gasses to and from the chamber, past corresponding sensors.

FIGS. 19a through 19c show bottom, side and side cross-sectional views, respectively, of a preferred skin capsule 130 of this invention. In particular, the inlet and outlet ports 132a and 132b, respectively, can be seen. Also shown, in side view, is recessed groove 134 into which an o-ring can be positioned in order to provide a scaled fit with iontophoresis chemical chamber. Also shown are screw holes 136 for use in assembling this portion of the component to a capsule body and cover as described herein. Seen in the side views is the substantially disc-shaped chamber itself, shown as 138, formed by the sidewalls of the capsule portion and the skin itself.

Figure 20B:
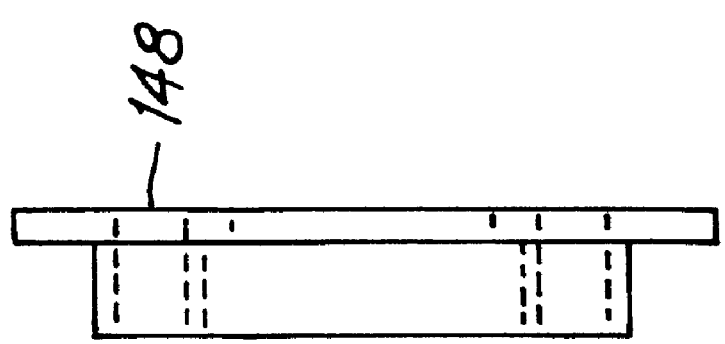
FIGS. 20a and 20b show top and side views, respectively, of a preferred iontophoresis chemical chamber of this invention.
Figure 20A:
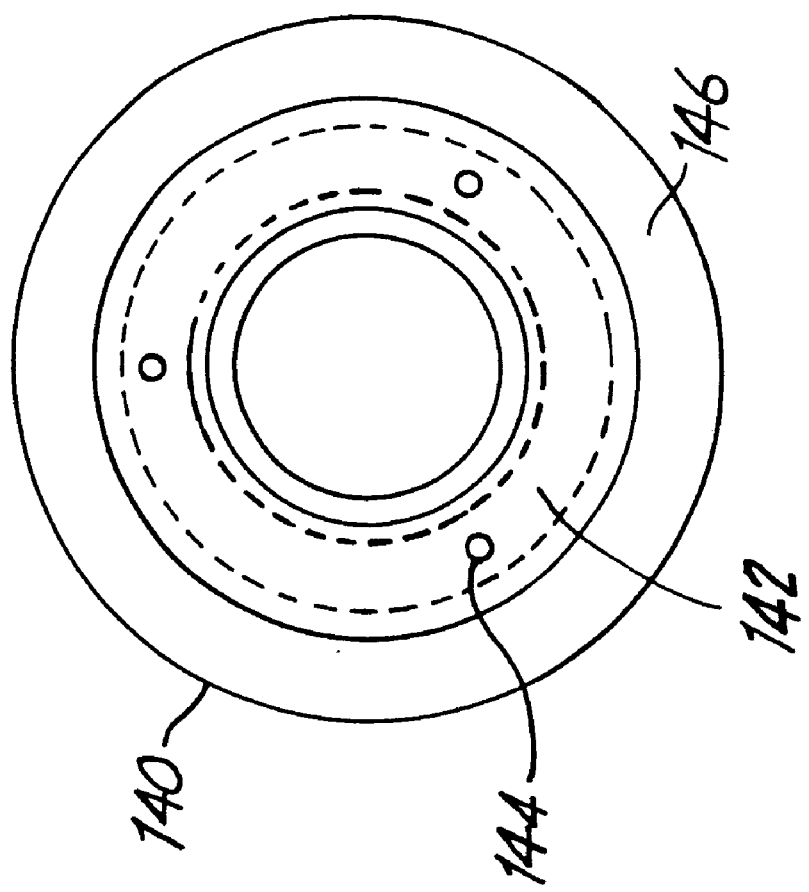

FIGS. 20a and 20b show top and side views, respectively, of a preferred iontophoresis chemical chamber 140 of this invention. The chamber can be seen to include the outer flange 146, surrounding a concentric raised portion 142 adapted to contain the stimulating agent. The raised portion provides a substantially open face 148 adapted to be contacted with the skin for the deliver of the agent thereto. Also shown are conductive metal rivets 144, for providing electrical contact to the gel.

Figure 17:
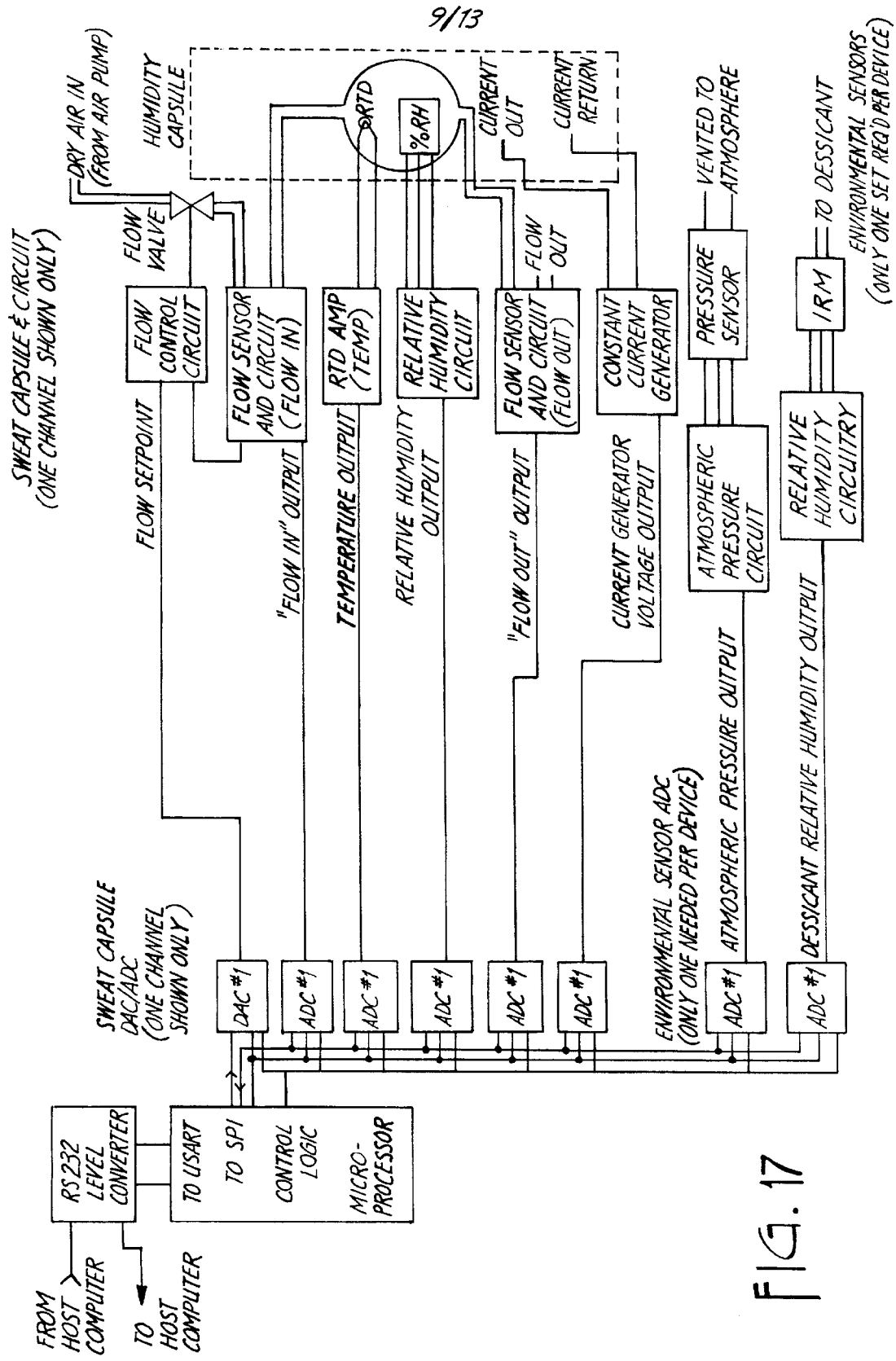
FIG. 17 is a system block diagram for the present invention.
Figure 21:
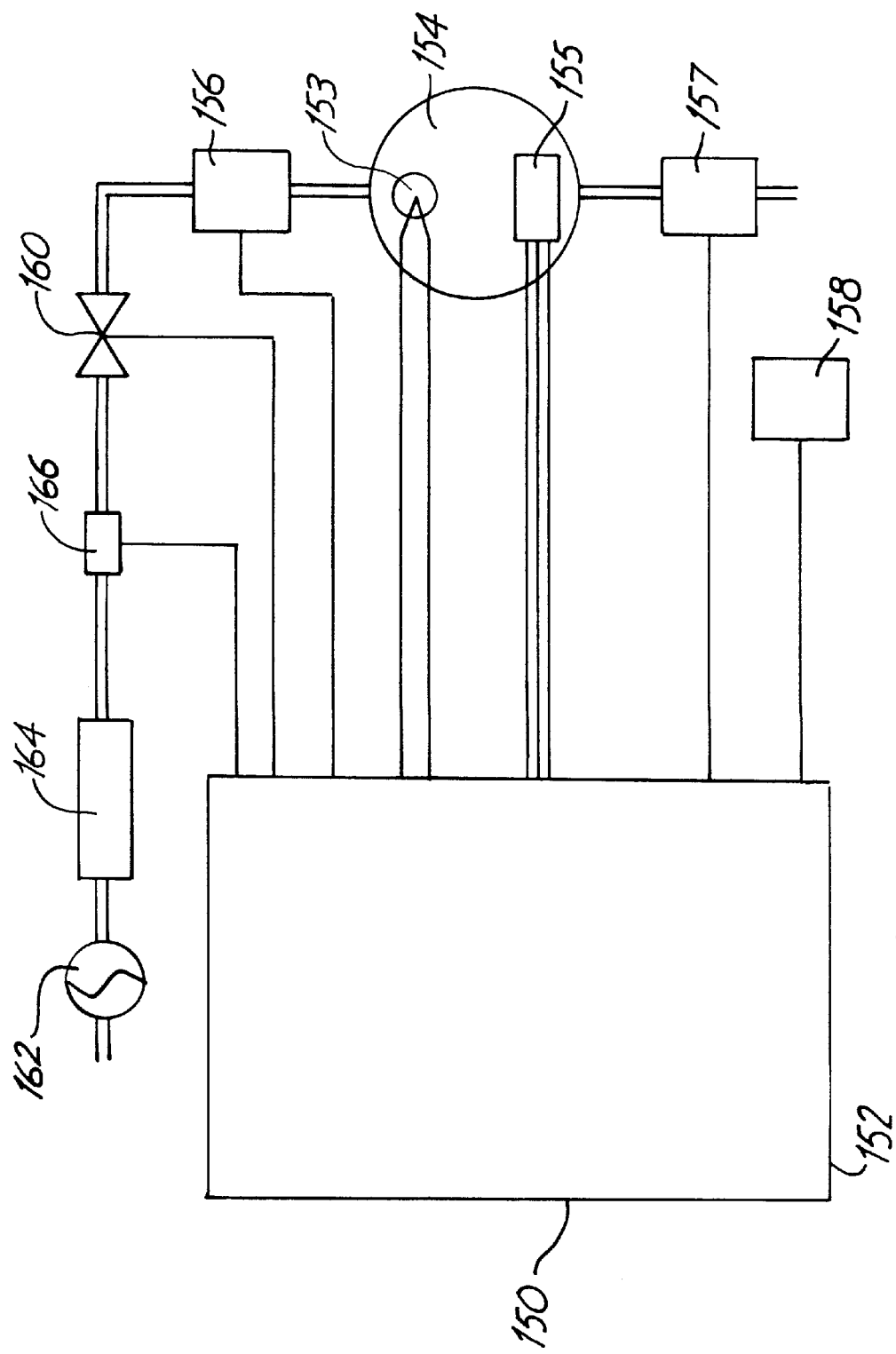
FIG. 21 shows a system block diagram, showing fundamental features of the diagram provided as FIG. 17.

FIG. 21 shows a system block diagram, showing fundamental features of the diagram provided as FIG. 17. The overall system 150 includes a controller 152 operably connected to a capsule assembly 154 that includes both a temperature sensor 153 and humidity sensor 155, each being operably coupled to a respective flow sensor and circuit 156 (flow in) and 157 (flow out). As shown, the system includes an atmospheric pressure sensor and circuit 158, as well as a flow control valve 160 operably coupled to an air pump 162 and desiccant pack 164, as well as humidity sensor 164 for sampling the dessicated air.

The present invention provides an apparatus and method for evoking and capturing a sweat sample. The apparatus 10 generally comprises a controller box or main unit 12, at least one skin capsule 14, an iontophoretic chemical chamber 16 for each skin capsule 14, a parking fixture 18 for each available channel 20, one "wet" cell, a removable disposable desiccant chamber 20 for each parking fixture 18, and an iontophoretic stimulator grounding pad 24 for each skin capsule. There are preferably four skin capsules 14 that correspond to four channels 20 in the main unit 12. The main unit 12 is electrically connected to a personal computer. ATLAS (Autonomic Testing Lab and Acquisition System) application software operating on the computer controls the operation of reading and processing the moisture measurement information provided by the main unit 12, including flow in, flow out, temperature, humidity, desiccant humidity, and atmospheric pressure, and then calculates the sweat rate and total sweat volume.

The apparatus and method for evoking and capturing a sweat sample is further described and shown in the attached Quantitative Sudomotor Axon Reflex Tester Version R (QSART II) 510K Application, Quantitative Sudomotor Axon Reflex Tester Version H (QSART II) Hardware User Guide, and the Autonomic Test Lab Acquisition System (ATLAS) Software User Guide which are hereby incorporated by reference as part of the specification.

The main unit 12 contains a power supply, an air pump, an airflow regulator, a voltage sensitive proportioning orifice valve, mass air flow sensors, a source-air desiccant pack 22, output air connections 26, input air connections 28, an iontophoretic stimulator circuit, and a DB serial port.

The iontophoretic chemical chambers 16 are made to hold the chemical stimulating agent. These chambers, once filled, are snapped onto the skin-side of the skin capsules 14. The chamber 16 is a ring-shaped chamber that is open on the skin side. Thus, when the chamber 16 is attached to the skin capsule 14 and the capsule 14 is affixed to the skin, the stimulating agent is iontophoresed into the skin directly surrounding the area being tested. The stimulating agent is blended into an agarose gel which has been previously poured into the chamber and allowed to solidify. Thus the finished gel component is shaped like a donut which is held in place on three sides by the chamber. The concentration of acetylcholine is 0.5 molar solution suspended in a 1.5% agarose gel. The open end of the chamber is then covered with an individual protective wrap for storage purposes. When the chamber is to be used, the technician removes the individual protective wrapping from the chamber, affixes the chamber to the skin capsule, and affixes the chamber/capsule assembly to the patient's skin. The gel will remain in the chamber until it is iontophoresed into the skin. The iontophoretic chemical chambers are single-use only components and are disposed of via the biohazard waste stream in accordance to the laws, regulations, and procedures in effect at the user's facility.

The humidity-measuring sensors in the skin capsules 14 will record any moisture that is found, whether due to room humidity or water being given off by the skin. Therefore a dry air source is used (from the desiccant pack), and the skin capsules are parked on the parking fixture when not in use.

Each of the parking fixtures 18 also contain a removable, disposable desiccant chamber 22 in order to keep the sensor dry when not in use. It is possible to obtain a calibration verifications plot for zero moisture by running a QSART test with the capsule parked on the parking fixtures The apparatus of the present invention is also provided with a wet cell so that 100% relative humidity can be measured for calibration verification purposes.

The iontophoretic grounding pads 24 are self adhesive pads which are commonly available on the market such as the Life-Tech model 6585S or equivalent. In order to calculate the amount of humidity within the capsule, one must know both the temperature and relative humidity. These values are accurately provided by the sensors. The actual moisture is calculated according to natural gas laws. The apparatus of the present invention is calibrated to physical standards.

The apparatus of the present invention has four channels 20 allowing four individual moisture samples to be obtained simultaneously from a given patient. The entire process of taking four measurements simultaneously from a given patient can be completed in tinder thirty minutes.

The iontophoretic stimulus on and off control is provided by a switch for each channel. The switch illuminates a light when the channel is activated and does not illuminate the light when deactivated. The stimulus amplitude and duration might vary by the specific protocol, both the apparatus provides a fixed 2 mA constant current stimulus, with the duration controlled by the operator according to the physician's protocol. A commonly accepted method advocated is 2 niA of stimulation with acetylcholine for five minutes; then an additional five minutes without stimulation. This results in a ten minute test from which the rate and volume of both resting sweat and evoked sweat and the latency can be measured. Such a test is sensitive and reproducible in controls and in patients with diabetic peripheral neuropathy.

Performing a test using the apparatus of the present invention does not require the cognitive cooperation of the patient, other than to sit still during the test and to follow the technicians' basic instructions such as to roll up a sleeve. Therefore, the test is considered to be an objective rather than subjective test.

The object of testing is to obtain data which is not affected by confounding variables which are foreseeable or controllable by the technician. For example, loud, startling noises, fear of medical equipment, personnel, or institutions or embarrassing questioning could cause a patient to sweat abnormally, or to sweat too soon before a proper resting baseline is established. Scratching the skin near the site to be tested could also evoke a premature sweat response. The patient must not be abnormally dehydrated. As an extreme example, a cold compress for a patient who has a headache could conceivably impair sweat response. It is important that the patient be tested in his or her natural resting condition, being cognizant of situation where the patient may have exerted himself/herself on the way to the examining room which could result in some extra sweating as a result of exertion. A patient should have enough time to acclimate to room temperature before testing in either hot or cold weather. How quickly the patient acclimates to room temperature and the effect of not allowing enough time to acclimate will vary. A patient should be prepared the test by limiting the food or drugs, such as coffee or nicotine, consumed by the patient.

The steps of the test may include the following:

(1) Perform a visual check of the equipment, ensuring that fresh chemical chambers are available.

(2) Decide how many sites on the patients' body should be tested in order to determine how many channels will be used, and ensure that each of the capsule/hose assemblies are plugged into the controller box.

(3) Enter the patient's demographics in the ATLAS software on the personal computer.

(4) Select a skin area that is free of breaks, fissures, inflammation, or other observable abnormalities in the skin and that is relatively wrinkle-free and hairless such as the medial forearm, the proximal leg, the distal leg, and the proximal foot.

(5) Clean the selected skin area to remove dirt, fatty materials and loose dead cells using alcohol, distilled water, and a dry gauze pad so that the electrical impedance of the skin will be minimized.

(6) Attach the device to the patient by:
  (a) removing the stimulation chemical chamber from its storage container, removing protective coverings, and examining the underside of the chamber to ensure the gel is not dried out or cracked,
  (b) firmly pressing the chamber into place on the skin capsule ensuring the electrical contacts of the chamber are fully seated against the electrical contact of the skin capsule,
  (c) firmly affixing each assembly to the skin at the prepared site using a Velcro strap or some other fastener.
  (d) ensuring the iontophoretic chamber makes good uniform contact for even current distribution during iontophoretic stimulation, which ensures more comfortable stimulation and less chance of skin irritation.

(7) Apply an iontophoretic grounding electrode for each chamber/capsule assembly by:
  (a) locating a desired skin site for the electrode about three to six inches away from the site of iontophoreses, while avoiding areas where tendons or bone are palpable just beneath the skin such as near the wrist, and avoid placing the electrode across the chest,
  (b) preparing the skin sites by wiping the skin with alcohol and allowing to dry before affixing the electrode,
  (c) securing the grounding electrode firmly so that its gel surface is pressed flat against the skin to ensure good conductivity which minimizes patient discomfort.

(8) Record the sweat output using the ATLAS software.

(9) Observe the resting sweat output being plotted on the computer display, allowing the sweat rate to stabilize before beginning iontophoretic stimulation.

(10) Start the iontophoretic stimulation by pressing the "Enable Stimulation" button for the desired channel. The ATLAS software allows stimulation for a fixed time, but will not allow stimulation longer than ten minutes. Continue to record the natural evoked response until the end of the test period.

(11) Stop recording, disconnect patient remove and discard chemical chambers according to law, regulations, and procedures, and place the skin capsules back onto the parking fixture.

(12) Store or otherwise process the data using the ATLAS software to view and analyze the rate and volume curves.

The present invention provides an apparatus and method for evoking and capturing a sweat sample. The apparatus comprises a main unit having at least one channel, at least one skin capsule operably connected to the main unit, a chemical chamber removably attached to each of the skin capsules, a parking fixture for each of the channels, a removable, disposable desiccant chamber upon which each of the parking fixtures are mounted during non-use; and a stimulator grounding pad operably connected to each of the skin capsules. The method comprises the steps of deciding how many sites on the patients' body should be tested in order to determine how many channels will be used, and ensure that each of the capsule hose assemblies are plugged into the controller box, entering the patient's demographics on a personal computer, selecting a skin area that is free of breaks, fissures, inflammation, or other observable abnormalities in the skin and that is relatively wrinkle-free and hairless, cleaning the selected skin area to minimize the electrical impedance of the skin, attaching the device to the patient, recording the sweat output using the computer, observing the resting sweat output and allowing the sweat rate to stabilize before beginning iontophoretic stimulation, starting the iontophoretic stimulation by pressing the "Enable Stimulation" button for the desired channel, stopping recording, disconnecting the patient, removing the chemical chambers from the skin capsules, and placing the skin capsules back onto the parking fixture, and processing the recorded data using the computer to view and analyze rate and volume curves.

In one preferred embodiment, therefore, the invention provides an apparatus for evoking and capturing a sweat sample, comprising:
  (a) a main unit having at least one channel;
  (b) at least one skin capsule operably connected to the main unit,
  (c) a chemical chamber removably attached to each of the skin capsules;
  (d) a parking fixture for each of the channels;
  (e) a removable, disposable desiccant chamber upon which each of the parking fixtures are mounted during non-use; and
  (f) a stimulator grounding pad operably connected to each of the skin capsules.

The apparatus preferably includes a wet cell for measuring humidity. The apparatus also preferably includes a computer electrically connected to the main unit and an application software program operating on the computer, the application software calculating sweat rate and total sweat volume based on measurements provided by the main unit. The measurements can include flow in, flow out, temperature, humidity, desiccant humidity, and atmospheric pressure.

The main unit of the apparatus preferably includes a power supply, an air pump, an airflow regulator, a voltage sensitive proportioning orifice valve, mass air flow sensors, the desiccant pack, output air connections, input air connections, and iontophoretic stimulator circuit, and a serial port. In other preferred embodiments, the chambers are snapped onto the skin capsules, and a compact temperature sensor and a compact humidity sensor are positioned within the skin capsule.

The present invention further provides a corresponding method for evoking and capturing a sweat sample, comprising the steps of:

(1) deciding how many sites on the patients' body should be tested in order to determine how many channels will be used, and ensure that each of the capsule/hose assemblies are plugged into the controller box.

(2) entering the patient's demographics on a personal computer;

(3) selecting a skin area that is free of breaks, fissures, inflammation, or other observable abnormalities in the skin and that is relatively wrinkle-free and hairless;

(4) cleaning the selected skin area to minimize the electrical impedance of the skin;

(5) attaching the device to the patient;

(6) recording the sweat output using the computer;

(7) observing the resting sweat output and allowing the sweat rate to stabilize before beginning iontophoretic stimulation;.

(8) starting the iontophoretic stimulation by pressing the "Enable Stimulation" button for the desired channel;

(9) stopping recording, disconnecting the patient, removing the chemical chambers from the skin capsules, and placing the skin capsules back onto the parking fixture; and

(10) processing the recorded data using the computer to view and analyze rate and volume curves.

In such a method, the step of attaching the device to the patient preferably includes the steps of:

(1) removing the stimulation chemical chamber from its storage container, removing protective covering,s from the chamber, and examining the underside of the chamber to ensure the get is not dried out or cracked;

(2) firmly pressing the chamber into place on the skin capsule ensuring the electrical contacts of the chamber are fully seated against the electrical contact of the skin capsule;

(3) firmly affixing each assembly to the skin at the prepared site on the skin using a fastener;

(4) ensuring, the chamber makes good uniform contact for even current distribution during iontophoretic stimulation; and (5) applying an iontophoretic grounding electrode by:

(a) locating, a desired skin site for the electrode about three to six inches away from the site of iontophoreses, and avoiding areas where tendons or bone are palpable just beneath the skin such as near the wrist and avoid placing the electrode across the chest;

(b) preparing the skin sites by wiping the skin with alcohol and allowing to dry before affixing the electrode; and (c) securing, the grounding electrode firmly so that its gel surface is pressed flat against the skin to ensure good conductivity which minimizes patient discomfort.

The descriptions above and the accompanying materials should be interpreted in the illustrative and not the limited sense. While the invention has been disclosed in connection with the preferred embodiment or embodiments thereof, it should be understood that there may be other embodiments which fall within the scope of the invention.

What is claimed is:

1. An apparatus and method for evoking, capturing, and optionally measuring one or more parameters within a sweat sample, the apparatus comprising, a) at least one skin capsule comprising
   i) a capsule chamber adapted to be removably positioned in sealed contact with the skin, in order to contain sweat evoked from the underlying skin,
   ii) one or more sensors operably connected to the capsule chamber and adapted to measure corresponding parameters within the capsule chamber itself,
   iii) gas inlet and outlet conduits adapted to controllably deliver desiccated gas and recover gas from the capsule chamber, respectively, and
   iv) an electrical contact adapted to receive electrical energy from a controller in order to deliver the energy to a corresponding iontophoretic active electrode contact, b) at least one iontophoretic chemical chamber comprising
   i) a biocompatible polymeric material forming a chamber adapted to be removably retained upon the skin of a patient,
   ii) a stimulating agent stably retained within the chemical chamber in a manner that permits the agent to be make iontophoretic contact with the skin, and
   iii) an iontophoretic active electrode contact, adapted to make contact with the electrical contact of the skin capsule, in order to form an active electrode for the delivery of stimulating agent from the chemical chamber and to the skin,
   each chemical chamber being adapted to be affixed to a skin capsule in a manner that permits the resultant capsule/chemical chamber assembly to be operated in order to be positioned upon and evoke a sweat response from the skin, by iontophoretic delivery of the stimulating agent, and adapted, in turn, to contain a known volume of the sweat evoked, in the form of moisture within the capsule chamber, and c) a controller adapted to control and coordinate the operation of the apparatus, including the iontophoretic chemical chamber and sensors.

2. An apparatus according to claim 1 further comprising at least one wet cell adapted to permit comparison to a known humidity standard, in order to calibrate the apparatus.

3. An apparatus according to claim 2 further comprising a number of storage fixtures equal to the number of skin capsules plus wet cells.

4. An apparatus according to claim 3 further comprising at least one return electrode, containing an electrolyte solution and adapted to be positioned upon the patient's skin, preferably in an area remote from the chemical capsule, in order to permit iontophoresis of the stimulating agent by the application of direct current to the active electrode.

5. An apparatus according to claim 1 wherein the controller is a four channel controller and the apparatus comprises four skin capsules, and four corresponding iontophoretic chemical chambers.

6. An apparatus according to claim 1 wherein the stimulating agent is provided in the form of a gel and comprises acetylcholine.

7. An apparatus for capturing and measuring one or more parameters within a sweat sample, the apparatus comprising, a) at least one skin capsule comprising
  i) a capsule chamber adapted to be removably positioned in sealed contact with the skin, in order to contain sweat evoked from the underlying skin,
  ii) one or more sensors operably connected to the capsule chamber and adapted to measure corresponding parameters within the capsule chamber itself; and
  iii) gas inlet and outlet conduits adapted to controllably deliver desiccated gas and recover gas from the capsule chamber, respectively, and
b) a controller adapted to control and coordinate the operation of the apparatus.

8. An apparatus according to claim 7 in combination with an exercise device, wherein the apparatus is adapted to capture and measure one or more parameters with in sweat produced in the course of exercise.

9. An apparatus according to claim 8 wherein the apparatus is provided in a form adapted to retrofit an existing exercise device.

10. An apparatus according to claim 8 wherein the apparatus is provided as an integral part of an exercise device.

11. A method for evoking, capturing, and optionally measuring one or more parameters within a sweat sample, the method comprising a) providing an apparatus according to claim 1, b) affixing the skin capsule(s) to the skin of a patient, c) affixing the iontophoretic chemical chamber(s) to corresponding skin capsules, c) operating the apparatus in order to evoke a sweat response and to determine one or more parameters within the evoked sweat by using of the sensor(s) within the skin capsule(s).

12. A method according to claim 11 wherein the method is used to measure and compare both resting sweat output and evoked sweat output, both in terms of both rate and volume.

* * * * *